(12) United States Patent
Levine et al.

(10) Patent No.: US 7,766,973 B2
(45) Date of Patent: Aug. 3, 2010

(54) EVERSION RESISTANT SLEEVES

(75) Inventors: Andy H. Levine, Newton, MA (US);
David A. Melanson, Hudson, NH (US);
Ian Parker, Bristol, RI (US)

(73) Assignee: GI Dynamics, Inc., Lexington, MA (US)

( * ) Notice: Subject to any disclaimer, the term of this patent is extended or adjusted under 35 U.S.C. 154(b) by 1451 days.

(21) Appl. No.: 11/147,984

(22) Filed: Jun. 8, 2005

(65) Prior Publication Data
US 2006/0161187 A1 Jul. 20, 2006

Related U.S. Application Data

(60) Provisional application No. 60/645,296, filed on Jan. 19, 2005, provisional application No. 60/662,570, filed on Mar. 17, 2005.

(51) Int. Cl.
*A61F 2/04* (2006.01)
*A61M 5/00* (2006.01)

(52) U.S. Cl. .................. 623/23.7; 623/23.64; 604/8

(58) Field of Classification Search ... 623/23.64–23.68, 623/1.24–1.26, 1.12–1.13, 23.7, 2.14, 2.18; 604/8
See application file for complete search history.

(56) References Cited

U.S. PATENT DOCUMENTS

| | | | |
|---|---|---|---|
| 4,246,893 A | 1/1981 | Berson | |
| 4,265,694 A | 5/1981 | Boretos et al. | |
| 4,271,827 A | 6/1981 | Angelchik | |
| 4,315,509 A | 2/1982 | Smit | |
| 4,341,218 A | 7/1982 | U | |
| 4,617,932 A | 10/1986 | Kornberg | |
| 4,768,507 A | 9/1988 | Fischell et al. | |
| 4,846,836 A | 7/1989 | Reich | |
| 4,905,693 A | 3/1990 | Ravo | |

(Continued)

FOREIGN PATENT DOCUMENTS

EP   0 506 918 B1   1/1996

(Continued)

OTHER PUBLICATIONS

Rubino, F., et al., "Potential of Surgery for Curing Type 2 Diabetes Mellitus," *Annals of Surgery*, 236(5):554-559 (2002).

(Continued)

*Primary Examiner*—Alvin J. Stewart
(74) *Attorney, Agent, or Firm*—Hamilton, Brook, Smith & Reynolds, P.C.

(57) ABSTRACT

The invention relates to improved means for preventing eversion and subsequent obstruction of thin-walled, floppy gastrointestinal liners implanted in the digestive tract of an animal. The implantable devices include an anchor adapted for attachment within a natural body lumen and a thin-walled, floppy sleeve open at both ends and defining a lumen therebetween. A substantial length of the sleeve has material characteristics that result in the sleeve being prone to eversion in the presence of retrograde pressures. Exemplary eversion-resistant features provide an increased stiffness and/or an increased friction coefficient between the anchor and the proximal end of the sleeve to resist eversion. In some embodiments, the eversion-resistant feature includes an anti-buckling element, such as a wire coupled along the substantial length of the sleeve.

25 Claims, 10 Drawing Sheets

U.S. PATENT DOCUMENTS

| | | | |
|---|---|---|---|
| 4,913,141 A | 4/1990 | Hillstead | |
| 5,037,387 A | 8/1991 | Quinn et al. | |
| 5,059,166 A | 10/1991 | Fischell et al. | |
| 5,104,399 A | 4/1992 | Lazarus | |
| 5,123,917 A | 6/1992 | Lee | |
| 5,135,516 A | 8/1992 | Sahatjian et al. | |
| 5,152,782 A | 10/1992 | Kowligi et al. | |
| 5,176,617 A | 1/1993 | Fischell et al. | |
| 5,226,429 A | 7/1993 | Kuzmak | |
| 5,254,133 A | 10/1993 | Seid | |
| 5,290,294 A | 3/1994 | Cox et al. | |
| 5,306,300 A | 4/1994 | Berry | |
| 5,314,473 A | 5/1994 | Godin | |
| 5,316,023 A * | 5/1994 | Palmaz et al. | 128/898 |
| 5,322,501 A | 6/1994 | Mahmud-Durrani | |
| 5,330,500 A | 7/1994 | Song | |
| 5,389,090 A | 2/1995 | Fischell et al. | |
| 5,405,378 A | 4/1995 | Strecker | |
| 5,423,851 A | 6/1995 | Samuels | |
| 5,476,506 A * | 12/1995 | Lunn | 623/1.28 |
| 5,480,423 A | 1/1996 | Ravenscroft et al. | |
| 5,492,530 A | 2/1996 | Fischell et al. | |
| 5,500,014 A * | 3/1996 | Quijano et al. | 623/1.24 |
| 5,562,728 A * | 10/1996 | Lazarus et al. | 623/1.14 |
| 5,605,530 A | 2/1997 | Fischell et al. | |
| 5,607,442 A | 3/1997 | Fischell et al. | |
| 5,634,928 A | 6/1997 | Fischell et al. | |
| 5,639,274 A | 6/1997 | Fischell et al. | |
| 5,643,312 A | 7/1997 | Fischell et al. | |
| 5,669,932 A | 9/1997 | Fischell et al. | |
| 5,695,516 A | 12/1997 | Fischell et al. | |
| 5,697,971 A | 12/1997 | Fischell et al. | |
| 5,722,984 A | 3/1998 | Fischell et al. | |
| 5,730,698 A | 3/1998 | Fischell et al. | |
| 5,733,325 A | 3/1998 | Robinson et al. | |
| 5,735,859 A | 4/1998 | Fischell et al. | |
| 5,735,892 A | 4/1998 | Myers et al. | |
| 5,743,874 A | 4/1998 | Fischell et al. | |
| 5,749,825 A | 5/1998 | Fischell et al. | |
| 5,759,174 A | 6/1998 | Fischell et al. | |
| 5,792,144 A | 8/1998 | Fischell et al. | |
| 5,792,172 A | 8/1998 | Fischell et al. | |
| 5,820,584 A | 10/1998 | Crabb | |
| 5,830,229 A | 11/1998 | Konya et al. | |
| 5,840,009 A | 11/1998 | Fischell et al. | |
| 5,843,164 A | 12/1998 | Frantzen et al. | |
| 5,855,601 A | 1/1999 | Bessler et al. | |
| 5,876,445 A | 3/1999 | Andersen et al. | |
| 5,879,282 A | 3/1999 | Fischell et al. | |
| 5,879,370 A | 3/1999 | Fischell et al. | |
| 5,910,145 A | 6/1999 | Fischell et al. | |
| 5,913,895 A | 6/1999 | Burpee et al. | |
| 5,919,233 A | 7/1999 | Knopf et al. | |
| 5,925,063 A | 7/1999 | Khosravi | |
| 5,962,620 A | 10/1999 | Reich et al. | |
| 5,976,153 A | 11/1999 | Fischell et al. | |
| 6,013,019 A | 1/2000 | Fischell et al. | |
| 6,027,508 A | 2/2000 | Ren et al. | |
| 6,027,526 A | 2/2000 | Limon et al. | |
| 6,086,604 A | 7/2000 | Fischell et al. | |
| 6,102,887 A | 8/2000 | Altman | |
| 6,120,533 A | 9/2000 | Fischell | |
| 6,120,534 A | 9/2000 | Ruiz | |
| 6,146,323 A | 11/2000 | Fischell | |
| 6,152,956 A * | 11/2000 | Pierce | 623/1.13 |
| 6,179,868 B1 | 1/2001 | Burpee et al. | |
| 6,187,016 B1 | 2/2001 | Hedges et al. | |
| 6,190,403 B1 | 2/2001 | Fischell et al. | |
| 6,221,043 B1 | 4/2001 | Fischell et al. | |
| 6,221,102 B1 | 4/2001 | Baker et al. | |
| 6,241,757 B1 | 6/2001 | An et al. | |
| 6,251,064 B1 | 6/2001 | Silverman et al. | |
| 6,270,521 B1 | 8/2001 | Fischell et al. | |
| 6,302,891 B1 | 10/2001 | Nadal | |
| 6,302,917 B1 | 10/2001 | Dua et al. | |
| 6,315,708 B1 | 11/2001 | Salmon et al. | |
| 6,355,056 B1 | 3/2002 | Pinheiro | |
| 6,356,782 B1 | 3/2002 | Sirimanne et al. | |
| 6,375,660 B1 | 4/2002 | Fischell et al. | |
| 6,383,214 B1 | 5/2002 | Banas et al. | |
| 6,401,718 B1 | 6/2002 | Johnson et al. | |
| 6,402,779 B1 | 6/2002 | Colone et al. | |
| 6,406,792 B1 | 6/2002 | Briquet et al. | |
| 6,485,515 B2 | 11/2002 | Strecker | |
| 6,520,985 B1 | 2/2003 | Burpee et al. | |
| 6,540,775 B1 | 4/2003 | Fischell et al. | |
| 6,540,789 B1 | 4/2003 | Silverman et al. | |
| 6,544,291 B2 * | 4/2003 | Taylor | 623/23.68 |
| 6,547,817 B1 | 4/2003 | Fischell et al. | |
| 6,558,429 B2 | 5/2003 | Taylor | |
| 6,623,518 B2 | 9/2003 | Thompson et al. | |
| 6,635,069 B1 | 10/2003 | Teoh et al. | |
| 6,635,079 B2 | 10/2003 | Unsworth et al. | |
| 6,645,239 B1 | 11/2003 | Park et al. | |
| 6,652,555 B1 | 11/2003 | VanTassel et al. | |
| 6,669,722 B2 | 12/2003 | Chen et al. | |
| 6,675,809 B2 | 1/2004 | Stack et al. | |
| 6,676,692 B2 | 1/2004 | Rabkin et al. | |
| 6,699,278 B2 | 3/2004 | Fischell et al. | |
| 6,706,061 B1 | 3/2004 | Fischell et al. | |
| 6,709,450 B2 * | 3/2004 | Kang et al. | 623/1.13 |
| 6,716,240 B2 | 4/2004 | Fischell et al. | |
| 6,736,840 B2 | 5/2004 | Fischell et al. | |
| 6,740,121 B2 | 5/2004 | Geitz | |
| 6,764,518 B2 | 7/2004 | Godin | |
| 6,773,440 B2 | 8/2004 | Gannoe et al. | |
| 6,776,791 B1 | 8/2004 | Stallings et al. | |
| 6,802,868 B2 | 10/2004 | Silverman et al. | |
| 6,821,291 B2 | 11/2004 | Bolea et al. | |
| 6,845,776 B2 | 1/2005 | Stack et al. | |
| 6,860,901 B1 | 3/2005 | Baker et al. | |
| 6,936,065 B2 | 8/2005 | Khan et al. | |
| 6,960,233 B1 | 11/2005 | Berg et al. | |
| 7,011,673 B2 | 3/2006 | Fischell et al. | |
| 7,025,791 B2 | 4/2006 | Levine et al. | |
| 7,037,327 B2 | 5/2006 | Salmon et al. | |
| 7,037,344 B2 | 5/2006 | Kagan et al. | |
| 7,081,132 B2 | 7/2006 | Cook et al. | |
| 7,087,088 B2 | 8/2006 | Berg et al. | |
| 7,121,283 B2 | 10/2006 | Stack et al. | |
| 7,122,058 B2 | 10/2006 | Levine et al. | |
| 7,146,984 B2 * | 12/2006 | Stack et al. | 128/898 |
| 7,152,607 B2 | 12/2006 | Stack et al. | |
| 7,160,312 B2 | 1/2007 | Saadat | |
| 7,175,660 B2 | 2/2007 | Cartledge et al. | |
| 7,211,114 B2 | 5/2007 | Bessler et al. | |
| 7,220,237 B2 | 5/2007 | Gannoe et al. | |
| 7,220,284 B2 | 5/2007 | Kagan et al. | |
| 7,267,694 B2 | 9/2007 | Levine et al. | |
| 7,314,489 B2 | 1/2008 | McKenna et al. | |
| 7,316,716 B2 * | 1/2008 | Egan | 623/23.65 |
| 7,329,285 B2 | 2/2008 | Levine et al. | |
| 7,338,520 B2 | 3/2008 | Bailey et al. | |
| 7,347,875 B2 | 3/2008 | Levine et al. | |
| 7,354,454 B2 | 4/2008 | Stack et al. | |
| 7,476,256 B2 | 1/2009 | Meade et al. | |
| 2001/0020190 A1 | 9/2001 | Taylor | |
| 2002/0022853 A1 | 2/2002 | Swanson et al. | |
| 2002/0032487 A1 | 3/2002 | Dua et al. | |
| 2002/0065545 A1 | 5/2002 | Leonhardt et al. | |
| 2002/0091439 A1 | 7/2002 | Baker et al. | |
| 2002/0099439 A1 * | 7/2002 | Schwartz et al. | 623/1.24 |
| 2002/0107565 A1 * | 8/2002 | Greenhalgh | 623/1.24 |
| 2002/0147489 A1 | 10/2002 | Hong et al. | |

| | | | |
|---|---|---|---|
| 2002/0177890 A1* | 11/2002 | Lenker ...................... 623/1.12 |
| 2002/0183786 A1 | 12/2002 | Girton |
| 2002/0188344 A1 | 12/2002 | Bolea et al. |
| 2003/0009236 A1* | 1/2003 | Godin ...................... 623/23.68 |
| 2003/0040808 A1 | 2/2003 | Stack et al. |
| 2003/0055492 A1* | 3/2003 | Shaolian et al. ............ 623/1.24 |
| 2003/0109931 A1 | 6/2003 | Geitz |
| 2003/0191476 A1 | 10/2003 | Smit |
| 2003/0199991 A1 | 10/2003 | Stack et al. |
| 2003/0216749 A1 | 11/2003 | Ishikawa et al. |
| 2004/0019388 A1 | 1/2004 | Starkebaum |
| 2004/0037865 A1 | 2/2004 | Miller |
| 2004/0039452 A1 | 2/2004 | Bessler |
| 2004/0082963 A1 | 4/2004 | Gannoe et al. |
| 2004/0092892 A1 | 5/2004 | Kagan et al. |
| 2004/0092974 A1 | 5/2004 | Gannoe et al. |
| 2004/0093065 A1 | 5/2004 | Yachia et al. |
| 2004/0107004 A1 | 6/2004 | Levine et al. |
| 2004/0117004 A1 | 6/2004 | Osborne et al. |
| 2004/0117031 A1 | 6/2004 | Stack et al. |
| 2004/0122470 A1 | 6/2004 | Deem et al. |
| 2004/0138761 A1 | 7/2004 | Stack et al. |
| 2004/0151740 A1 | 8/2004 | Aoki et al. |
| 2004/0158229 A1 | 8/2004 | Quinn |
| 2004/0172142 A1 | 9/2004 | Stack et al. |
| 2004/0181242 A1 | 9/2004 | Stack et al. |
| 2004/0193093 A1 | 9/2004 | Desmond, III |
| 2004/0193261 A1 | 9/2004 | Berreklouw |
| 2004/0210243 A1 | 10/2004 | Gannoe et al. |
| 2004/0220682 A1 | 11/2004 | Levine et al. |
| 2004/0236401 A1 | 11/2004 | Shin et al. |
| 2004/0249362 A1 | 12/2004 | Levine et al. |
| 2004/0260389 A1* | 12/2004 | Case et al. ................ 623/1.24 |
| 2005/0004681 A1 | 1/2005 | Stack et al. |
| 2005/0043601 A1 | 2/2005 | Kilcoyne et al. |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080491 A1 | 4/2005 | Levine et al. |
| 2005/0085787 A1 | 4/2005 | Laufer |
| 2005/0085923 A1 | 4/2005 | Levine et al. |
| 2005/0090873 A1 | 4/2005 | Imran |
| 2005/0096750 A1 | 5/2005 | Kagan et al. |
| 2005/0111072 A1 | 5/2005 | Miyagaki et al. |
| 2005/0125020 A1 | 6/2005 | Meade et al. |
| 2005/0125075 A1 | 6/2005 | Meade et al. |
| 2005/0137681 A1* | 6/2005 | Shoemaker et al. ........ 623/1.23 |
| 2005/0149114 A1 | 7/2005 | Cartledge et al. |
| 2005/0171556 A1 | 8/2005 | Murphy |
| 2005/0182483 A1* | 8/2005 | Osborne et al. ............ 623/1.24 |
| 2005/0192614 A1 | 9/2005 | Binmoeller |
| 2005/0216040 A1 | 9/2005 | Gertner et al. |
| 2005/0216042 A1 | 9/2005 | Gertner |
| 2005/0228415 A1 | 10/2005 | Gertner |
| 2005/0228504 A1 | 10/2005 | Demarais |
| 2005/0240279 A1 | 10/2005 | Kagan et al. |
| 2005/0256587 A1 | 11/2005 | Egan |
| 2005/0267405 A1 | 12/2005 | Shah |
| 2005/0267499 A1 | 12/2005 | Stack et al. |
| 2005/0267533 A1 | 12/2005 | Gertner |
| 2006/0009858 A1 | 1/2006 | Levine et al. |
| 2006/0064120 A1 | 3/2006 | Levine et al. |
| 2006/0106332 A1 | 5/2006 | Knudson et al. |
| 2006/0155312 A1 | 7/2006 | Levine et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0212042 A1 | 9/2006 | Lamport et al. |
| 2006/0265082 A1 | 11/2006 | Meade et al. |
| 2006/0271175 A1 | 11/2006 | Woolfson et al. |
| 2006/0287734 A1 | 12/2006 | Stack et al. |
| 2007/0005147 A1 | 1/2007 | Levine et al. |
| 2007/0010864 A1 | 1/2007 | Dann et al. |
| 2007/0027548 A1 | 2/2007 | Levine et al. |
| 2007/0032879 A1 | 2/2007 | Levine et al. |
| 2007/0049801 A1 | 3/2007 | Lamport et al. |
| 2007/0083271 A1 | 4/2007 | Levine et al. |
| 2008/0071383 A1 | 3/2008 | Levine et al. |
| 2008/0097466 A1 | 4/2008 | Levine et al. |
| 2008/0103604 A1 | 5/2008 | Levine et al. |
| 2008/0223476 A1 | 9/2008 | Stinson |
| 2008/0234834 A1 | 9/2008 | Meade et al. |

FOREIGN PATENT DOCUMENTS

| | | |
|---|---|---|
| EP | 0 857 471 A2 | 8/1998 |
| EP | 0935977 A2 | 8/1999 |
| EP | 0935977 A3 | 8/1999 |
| EP | 1481649 | 12/2004 |
| EP | 1 504 778 A2 | 3/2005 |
| EP | 1 504 778 A3 | 3/2005 |
| WO | WO 92/06734 A1 | 4/1992 |
| WO | WO 95/05132 | 2/1995 |
| WO | WO 97/03624 A1 | 2/1997 |
| WO | WO 98/22045 A | 5/1998 |
| WO | WO 99/23953 A | 5/1999 |
| WO | WO 99/44536 A | 9/1999 |
| WO | WO 00/32137 | 6/2000 |
| WO | WO 00/42945 | 7/2000 |
| WO | WO 01/12256 A1 | 2/2001 |
| WO | WO 01/35861 A1 | 5/2001 |
| WO | WO 02/081019 A1 | 10/2002 |
| WO | WO 02/096327 A2 | 12/2002 |
| WO | WO 03/017882 A2 | 3/2003 |
| WO | WO 03/086246 A1 | 10/2003 |
| WO | WO 03/086247 A1 | 10/2003 |
| WO | WO 2004/000169 A1 | 12/2003 |
| WO | WO 2004/004542 A2 | 1/2004 |
| WO | WO 2004/004542 A3 | 1/2004 |
| WO | WO 2004/014237 A1 | 2/2004 |
| WO | WO 2004/019765 A2 | 3/2004 |
| WO | WO 2004/019765 A3 | 3/2004 |
| WO | WO 2004/021894 A1 | 3/2004 |
| WO | WO 2004/037064 A2 | 5/2004 |
| WO | WO 2004/037064 A3 | 5/2004 |
| WO | WO 2004/049982 A2 | 6/2004 |
| WO | WO 2004/064682 A1 | 8/2004 |
| WO | WO 2004/069332 A1 | 8/2004 |
| WO | WO 2004/073782 A1 | 9/2004 |
| WO | WO 2004/080336 A2 | 9/2004 |
| WO | WO 2004/087014 A2 | 10/2004 |
| WO | WO 2004/087233 A2 | 10/2004 |
| WO | WO 2004/093639 A2 | 11/2004 |
| WO | WO 2004/093639 A3 | 11/2004 |
| WO | WO 2005/011533 A1 | 2/2005 |
| WO | WO 2005/060869 A1 | 7/2005 |
| WO | WO 2005/060882 A1 | 7/2005 |
| WO | WO 2005/082296 A1 | 9/2005 |
| WO | WO 2005/110280 A2 | 11/2005 |
| WO | WO 2005/110280 A3 | 11/2005 |
| WO | WO 2005/117716 A2 | 12/2005 |
| WO | WO 2005/118049 A1 | 12/2005 |
| WO | WO 2005/120363 | 12/2005 |
| WO | WO 2006/016894 AI | 2/2006 |
| WO | WO 2006/034062 A1 | 3/2006 |
| WO | WO 2006/078781 A1 | 7/2006 |
| WO | WO 2006/078927 A1 | 7/2006 |
| WO | WO2006/088578 A1 | 8/2006 |
| WO | WO 2006/102012 A1 | 9/2006 |

WO  WO 2006/133311 A2  12/2006

OTHER PUBLICATIONS

Rubino, F. and J. Marescaux, "Effect of Duodenal-Jejunal Exclusion in a Non-obese Animal Model of Type 2 Diabetes, A New Perspective for an Old Disease," *Annals of Surgery* 239(1)1-11, Jan. 2004.

CHOOSTENT™, Covered Esophageal Stent, Instructions, Retrieved from the Internet (http://mitech.co.kr/uploads/images/282/use guide esophachoo_english.pdf) on Jul. 26, 2005.

Hwang, J.C., et al., "Covered Retrievable Tracheobronchial Hinged Stent: An Experimental Study in Dogs," *J. Vasc. Interv. Radiol.*, 12(12):1429-1436 (Dec. 2001).

Irie, T., et al., "Relocatable Gianturco Expandable Metallic Stents[1]," *Radiology*, 178:575-578 (1991).

Lee, B.H., et al., "New Self-Expandable Spiral Metallic Stent: Preliminary clinical Evaluation in Malignant Biliary Obstruction," *J. Vasc Interv Radiol.*, 6(4):635-640 (Jul. 8, 1995).

Lee, S.H., "The Role of Oesophageal Stenting in the Non-Surgical Management of Oesophageal Strictures," *British J. Radiology*, 74:891-900 (Oct. 2001).

Shim, C.S., et al., "Fixation of a Modified Covered Esophageal Stent: Its Clinical Usefulness for Preventing Stent Migration," *Endoscopy*, 33(10):843-848 (Oct. 2001).

Song, H.Y., et al., "Benign and Malignant Esophageal Strictures: Treatment with a Polyurethane-Covered Retrievable Expandable Metallic Stent[1]," *Radiology*, 203(3):747-752 (Jun. 1997).

Song, H.Y., et al., "Covered Retrievable Expandable Nitinol Stents in Patients with Benign Esophageal Strictures: Initial Experience[1]," *Radiology*, 217:551-557 (Nov. 2000).

Song, H.Y., et al., "Tracheobronchial Strictures: Treatment with a Polyurethane-Covered Retrievable Expandable Nitinol Stent—Initial Experience," *Radiology*, 213:905-912 (Dec. 1999).

Yoon, C.J., et al., "Removal of Retrievable Esophageal and Gastrointestinal Stents: Experience in 113 Patients," *American J. of Roentgenology*, 183:1437-1444 (Nov. 2004).

International Search Report from related application PCT/US2008/013540 mailed on Mar. 26, 2009.

Written Opinion of the International Searching Authority from related application PCT/US2008/013540 mailed on Mar. 26, 2009.

\* cited by examiner

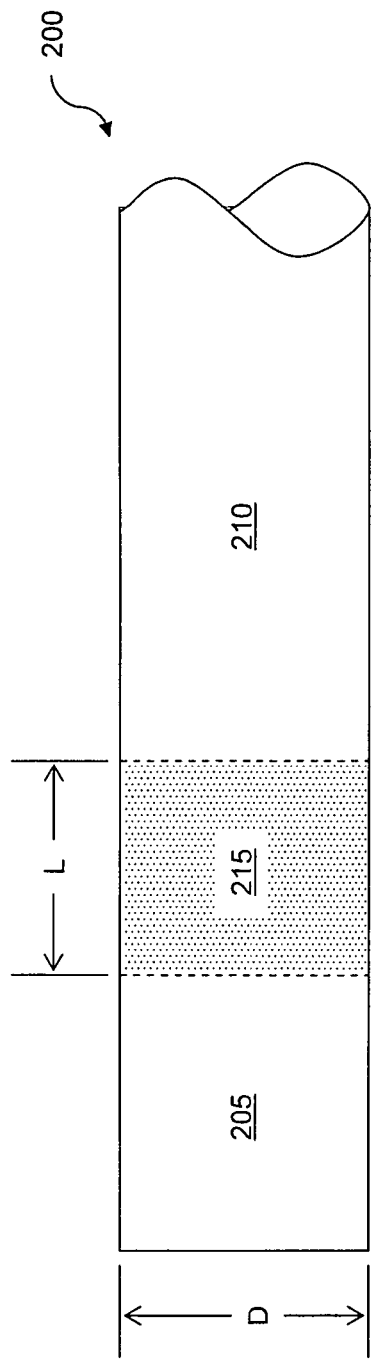
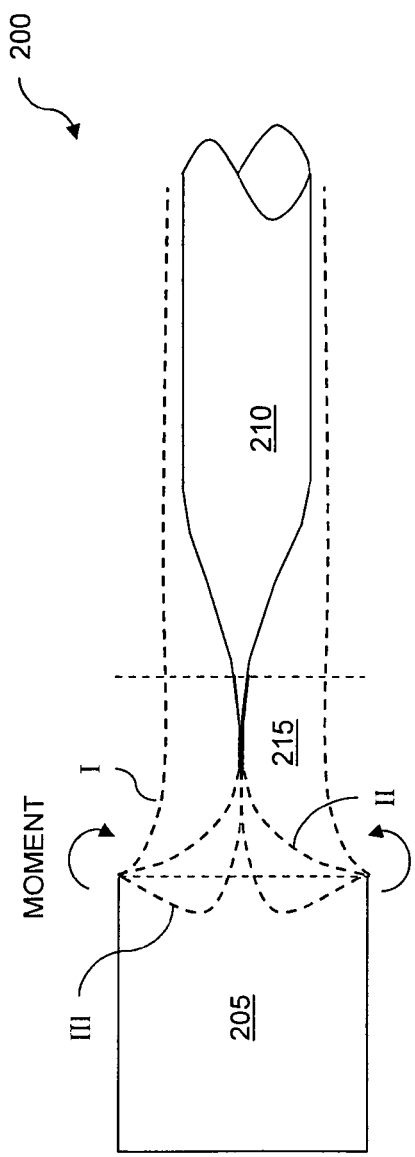
FIGURE 2A
FIGURE 2B

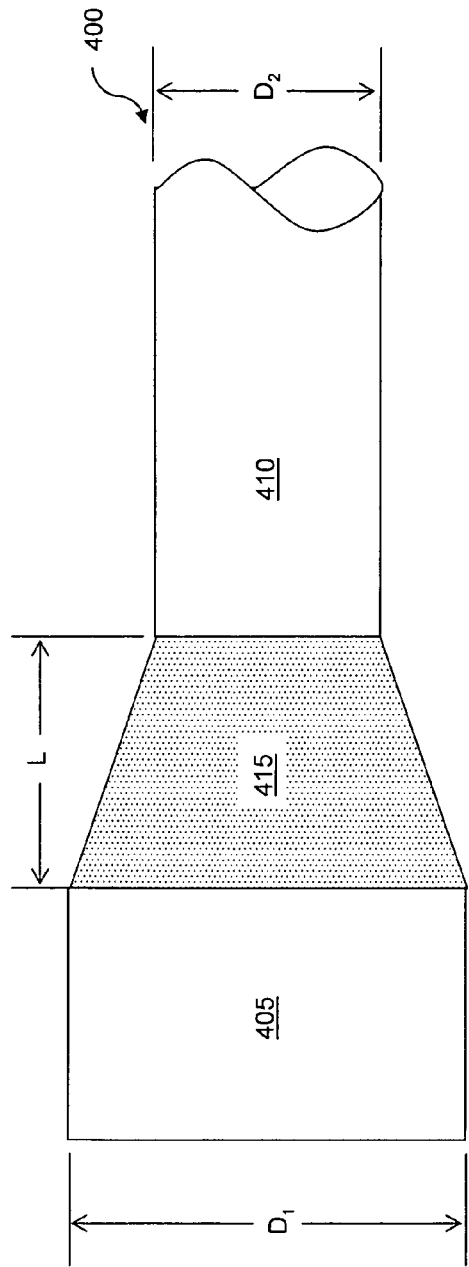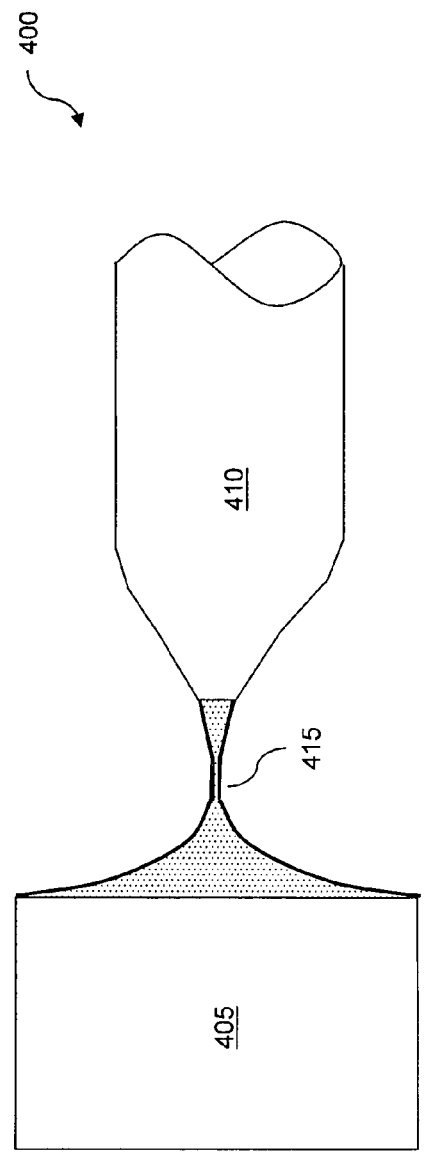
FIGURE 4A
FIGURE 4B

EVERSION RESISTANT SLEEVES

RELATED APPLICATIONS

This application claims the benefit of U.S. Provisional Application Nos. 60/645,296 filed on Jan. 19, 2005 and 60/662,570 filed on Mar. 17, 2005. The entire teachings of the above applications are incorporated herein by reference.

BACKGROUND OF THE INVENTION

According to the Center for Disease Control (CDC), over sixty percent of the United States population is overweight, and almost twenty percent are obese, presenting an overwhelming health problem. Moreover, obesity-related conditions cause as many as 280,000 deaths per year, generate $51 billion in annual US healthcare costs, and cause Americans to spend $33 billion per year on weight loss products. For example, one of the principle costs to the healthcare system stems from the co-morbidities associated with obesity. Type-2 diabetes has climbed to 7.3% of the population. Of those persons with Type-2 diabetes, almost half are clinically obese, and two thirds are approaching obese. Other co-morbidities include hypertension, coronary artery disease, hypercholesteremia, sleep apnea and pulmonary hypertension.

Two surgical procedures commonly performed that successfully produce long-term weight loss are the Roux-en-Y gastric bypass and the biliopancreatic diversion with duodenal switch (BPD). Both procedures reduce the size of the stomach plus shorten the effective-length of intestine available for nutrient absorption. However, these are serious surgical procedures with significant side effects, and thus they are reserved for the most morbidly obese.

Other devices to reduce absorption in the small intestines have been proposed (See U.S. Pat. No. 5,820,584 (Crabb), U.S. Pat. No. 5,306,300 (Berry) and U.S. Pat. No. 4,315,509 (Smit)). However, these devices are yet to be successfully implemented.

Examples of gastrointestinal sleeves have been described, which have great promise for treating obesity while minimizing the risks of surgery (See, for example, Meade et al., U.S. Utility application Ser. No. 10/858,851, filed Jun. 1, 2004; the entire teachings of which are incorporated herein by reference). It is important in any intestinal sleeve application to maintain patency of the device. When a sleeve is subjected to retrograde pressure, the sleeve may tend to evert (i.e., fold inward upon itself). Such eversions are undesirable and may lead to blockage, sleeve damage, and related complications. Thus, further improvements are desired to more fully realize the advantages which can be provided by gastrointestinal sleeves while minimizing any risk of complications.

SUMMARY OF THE INVENTION

There is a need for liners implantable within natural body lumens of an animal body. Moreover, there is a need for implantable sleeves that are thin-walled and floppy, yet resistant to eversion.

This invention relates to improved methods and devices for preventing eversion and subsequent obstruction of a thin-walled, floppy sleeve implant, anchored within a natural lumen of an animal body. The device may include an anchor adapted for attachment within a natural body lumen and a thin-walled, floppy sleeve open at both ends and defining a lumen therebetween. A substantial length of the sleeve material has one or more characteristics that result in the sleeve being prone to eversion. Such characteristics include thinness, floppiness and a low friction coefficient.

A particular application is anchoring gastrointestinal liners within the small intestine of an animal body. In some embodiments, the device includes an eversion-resistant feature disposed between the anchor and the proximal end of the sleeve adapted to inhibit eversion of the sleeve in the presence of retrograde pressures. The eversion-resistant feature may provide an increased stiffness relative to the sleeve's stiffness. Some ways of increasing stiffness include providing a different material that is stiffer than the sleeve itself. Alternatively, or in addition, the stiffness can be increased by providing an increased wall thickness relative to that of the sleeve. For example, thicker walls can be formed by using more than one layer of material (i.e., multiple layers of the sleeve material). Alternatively, or in addition, stiffness can be increased by providing a reinforcing member. For example, one or more soft, flexible wires can be coupled to the proximal end of the sleeve adjacent to the anchor.

In some embodiments, a surface of the eversion-resistant feature provides an increased coefficient-of-friction relative to that provided by the surface of the floppy sleeve itself. For example, the increased coefficient of friction can be provided using a different material than the sleeve. The different material may include a coating applied to a surface of the device. Alternatively or in addition, the increased coefficient of friction can be provided by texturing at least a portion of a surface of the sleeve. In either instance, the surface may be the interior surface, the exterior surface, or both the interior and exterior surfaces.

To inhibit eccentric eversions, the device may include a centering element adapted to focus collapse of the device just distal to the anchor towards the longitudinal axis of the anchor. For example, the centering element can include a sacrificial proximal portion, referred to as a "crumple zone" coupled to a distal reinforcing portion. The crumple zone is adapted to collapse in the presence of retrograde pressures before any substantial collapse of the reinforcing element.

Alternatively or in addition, the crumple zone can include a tapered segment, such as a tapered cone. The tapered segment defines a proximal opening having a first diameter and a distal opening having a second diameter that is less than the first. Retrograde pressures tend to move the distal opening proximally while tapering inhibits lateral movement towards the walls of the body lumen. Preferably, the eversion-resistant element is adapted to partially collapse upon itself thereby forming a valve allowing flow in an antegrade direction, while prohibiting flow in a retrograde direction, the valve enhancing the eversion-resistance performance of the sleeve.

The invention also relates to methods and devices that include an anchor adapted for attachment within a natural body lumen and a thin-walled, floppy sleeve open at both ends and defining a lumen therebetween. A substantial length of the sleeve has material characteristics that result in the sleeve being prone to eversion. The device also includes an eversion-resistant feature disposed along a substantial length of the sleeve adapted to inhibit eversion of the sleeve in the presence of retrograde pressures. In some embodiments, the eversion-resistant feature includes an anti-buckling member providing increased stiffness along the length of the sleeve. For example, the anti-buckling member can be a wire coupled along the length of the sleeve.

The invention also relates to methods and devices that include a floppy sleeve open at both ends defining a lumen therebetween and an anchor adapted for attaching at least a proximal portion of the sleeve within the small intestine of an animal body. A substantial length of the sleeve has material characteristics that result in the sleeve being prone to eversion. The device also includes an eversion-resistant feature. In some embodiments the eversion-resistant feature is disposed along a substantial length of the sleeve and is adapted to inhibit eversion of the sleeve in the presence of retrograde pressures. For example, the eversion-resistant feature may include an anti-buckling member, such as a wire, providing increased stiffness along the length of the sleeve. In other embodiments, the eversion-resistant feature is disposed between the anchor and a proximal length of the thin-walled, floppy sleeve.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 2A and 2B are schematic diagrams of an implantable anchored sleeve according to one embodiment of the invention;

FIGS. 4A and 4B are schematic diagrams of an exemplary implantable anchored sleeve according to one embodiment of the invention having a tapered section;

DETAILED DESCRIPTION OF THE INVENTION

A description of preferred embodiments of the invention follows.

Figure 1A:
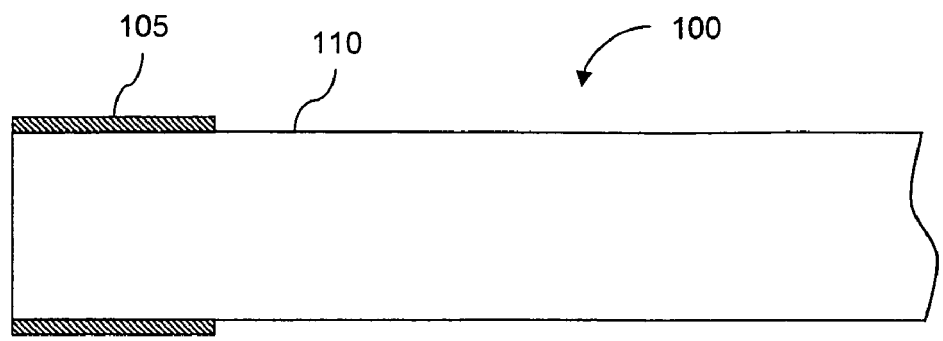
FIG. 1A is a cross-sectional diagram of an implantable anchored sleeve.

This invention relates to a method and device for implanting a sleeve within a natural body lumen of an animal, the sleeve including an anti-eversion feature to inhibit eversion of the sleeve when implanted. In particular, the invention relates to a bypass sleeve adapted for use within the digestive tract of an animal. Some examples of such intestinal implants are described in U.S. patent application Ser. No. 11/000,099, filed Nov. 30, 2004, and entitled "Bariatric Sleeve"; U.S. patent application Ser. No. 11/001,794, filed Nov. 30, 2004, and entitled "Methods of Treatment Using a Bariatric Sleeve"; U.S. patent application Ser. No. 10/726,011, filed Dec. 2, 2003, and entitled "Anti-Obesity Devices"; U.S. patent application Ser. No. 10/810,317, filed Mar. 26, 2004, and entitled "Enzyme Sleeve"; and U.S. patent application Ser. No. 10/811,293, filed Mar. 26, 2004, and entitled "Anti-Obesity Devices" all incorporated herein by reference in their entirety. As illustrated in FIG. 1A, an exemplary gastrointestinal sleeve 100 includes a sleeve anchor 105 coupled to the proximal end of an elongated, thin-walled, floppy sleeve 110. The sleeve is hollow with openings at both ends defining an interior lumen.

In this application, the sleeve is implanted within the intestine, such that chyme flowing within the intestine travels through the interior of the sleeve effectively bypassing that portion of the intestine. Preferably, the sleeve is thin-walled to so as to avoid irritating the intestine. Additionally, the thin-walled sleeve offers little resistance to peristaltic forces. Exemplary wall thicknesses are between 0.0003 and 0.0020 inches (i.e., 0.0076 and 0.051 mm).

Additionally, the sleeve material along the interior surface of the sleeve is smooth and slippery to avoid impeding the flow of chyme within the sleeve. Similarly, the exterior of the sleeve may also be smooth and slippery to promote the flow of material, such as digestive enzymes, between the exterior of the sleeve and the intestine wall. In some embodiments, the coefficient of friction of the sleeve material is about 0.2 or less.

The sleeve anchor is adapted for removable attachment thereby securing at least a proximal portion of the sleeve to the intestine. Although the sleeve may be attached anywhere within the intestine, it is preferably implanted in the small intestine, distal to the pyloric sphincter between the pylorus and the ampulla of vater, with the attached sleeve extending distally into the intestine for a predetermined length. An example of such a device is described in U.S. patent application Ser. No. 10/858,851, filed on Jun. 1, 2004 and entitled "Intestinal Sleeve," incorporated herein by reference in its entirety.

Although peristalsis provides a net resulting force directed antegrade from the stomach, there are times in the digestion cycle during which negative pressures or reverse peristalsis may occur. These negative or retrograde pressures may be the result of natural mixing waves, or other processes such as vomiting. The level of such pressures generated within the intestine are not well documented in the literature. Normal peristaltic pressures have been found to spike to 1.5-2.0 pounds-per-square-inch gauge (PSIG) (i.e., about 41.5-55.4 inches $H_2O$). It is expected that reverse peristalsis could produce similar spikes in pressure. If the pylorus is open, even slightly during this rise in pressure, there exists a driving force to push a gastrointestinal liner (i.e., sleeve) retrograde towards the stomach. Experiments in a porcine model have resulted in occasional vomiting that resulted in sleeve devices anchored in the duodenum to evert both through and around the anchor into the stomach. Once everted, the sleeve no longer functions and becomes obstructed.

Figure 1B:
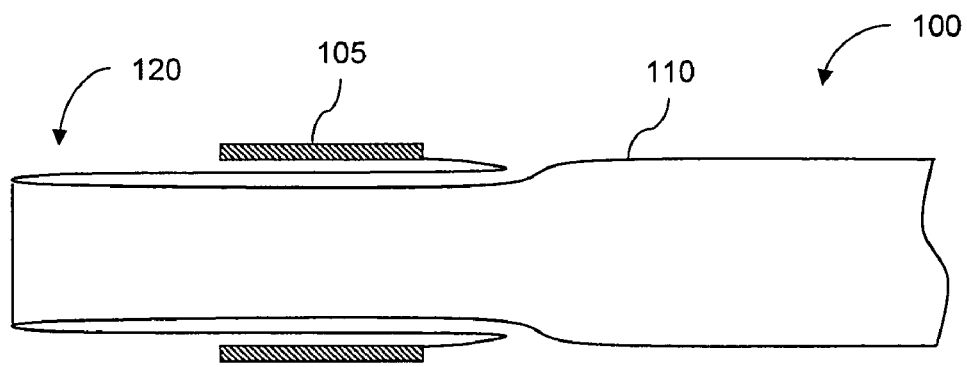
FIG. 1B is a cross-sectional diagram of the implantable anchored sleeve of FIG. 1A in a concentrically-everted state.
Figure 1C:
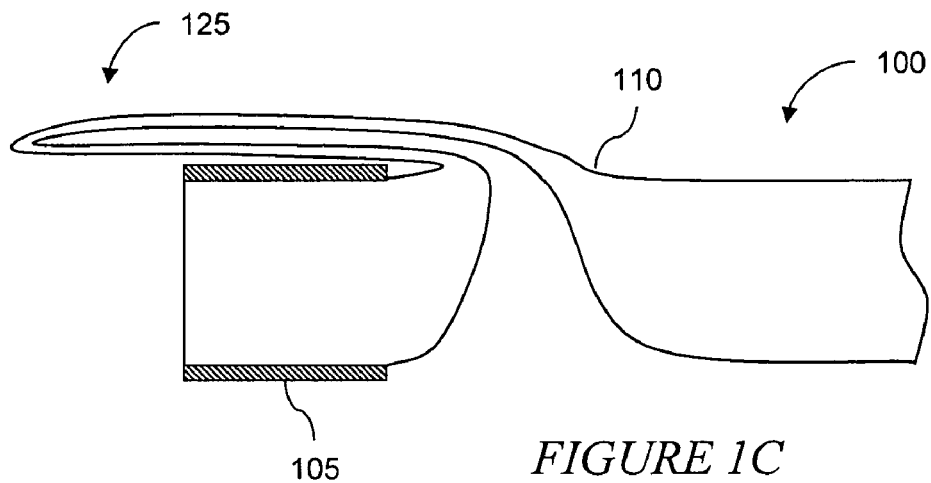
FIG. 1C is a cross-sectional diagram of the implantable anchored sleeve of FIG. 1A in a eccentrically-everted state.

The desirable features of being extremely thin-walled, floppy, and having a low friction coefficient all tend to make an intestinal sleeve more prone to eversion. At least two different eversion modes have been observed. A first eversion mode illustrated in FIG. 1B is referred to as a concentric eversion and is characterized by at least a portion of the sleeve 110 passing proximally through the center of the sleeve anchor 105. A second eversion mode illustrated in FIG. 1C is referred to as eccentric eversion and is characterized by at least a portion of the sleeve 110 passing proximally between the exterior surface of the anchor 105 and the interior surface (e.g., the tissue) of the body lumen within which the device 100 is implanted.

Eversions of a sleeve are more prone to occur when there is a relatively stiff section (e.g., the anchor) followed by a flexible section. The stiff section serves as a bending point or pivot for the flexible material resulting in a natural stress concentration. The stiff section must remain open during application of the pressure so the flexible material has an opening through which to evert. The present invention prevents such undesirable occurrences by providing a design feature that inhibits the sleeves from everting.

Eversion resistance can be accomplished by providing an "eversion resistant" feature. For example, an eversion-resistant feature may be provided at least at the transition between the anchor and the free sleeve as illustrated in FIG. 2A. As shown, a gastrointestinal implant 200 includes a sleeve anchor 205 at its proximal end followed by an elongated sleeve 210 at its distal end. An eversion-resistant feature 215 is provided at the transition between the anchor 205 and the sleeve 210.

As retrograde force and/or pressure increases, the walls of the eversion-resistant feature 215 may experience a moment of force about a pivot formed at the intersection of the relatively stiff anchor 205 and the more flexible eversion-resistant feature 215 (i.e., there is a tendency for the device to fold in upon itself as shown in FIG. 1B). Depending upon the magnitude of the force, the moment may tend to cause at least a partial rotation of the wall of the eversion-resistant feature 215. However, because the eversion-resistant feature 215 is adapted to resist eversion, rotation may be limited to substantially less than 90°. This initial bending phase is referred to herein as a pre-eversion phase and is schematically illustrated as phase I in FIG. 2B.

As the retrograde force and/or pressure increases, bending of the eversion-resistant feature may continue, approaching 90°, until at least some of the interior surfaces of the eversion-resistant feature come into contact with each other. When the interior of the eversion-resistant feature 215 collapses upon itself, it is referred to as a collapsed phase and is schematically illustrated as phase II. It is believed that the resulting structure formed by the at least partially collapsed sleeve provides enhanced eversion-resistance performance. Namely, a collapsed portion of the device gains additional reinforcement from the collapsed region due at least partially to rotated material from one side of the device pushing against similarly rotated material from another side. Thus, further rotation about the pivot of either side is at least partially inhibited by the opposite sides pushing against each other. A similar process is relied upon in reed-type valves sometimes referred to as "duckbill valves." Additionally, to the extent the surface material provides any non-insubstantial frictional coefficient, the resulting frictional force caused by overlapping layers of the material will resist movement of the material against itself and/or its surroundings, thereby inhibiting further eversion.

With an even greater retrograde force and/or pressure, bending of the eversion-resistant feature about the pivot may continue beyond 90°. As shown, the collapsed eversion-resistant feature 215 may begin to advance proximally into the interior aperture of the anchor 205. When a non-insignificant portion of the eversion-resistant feature 215 begins to advance proximally into the interior of the anchor 205, it is referred to as a partial-eversion phase and schematically illustrated as phase III. It is believed that the eversion-resistance performance remains enhanced during this phase as at least a portion of the device remains collapsed upon itself. Thus the reinforcing and/or frictional forces described above remain active. Consequently, there remains only a limited length of the device between the region of the collapse 215 and the pivot point, which limits partial eversion according to the length of this region. Of course, at sufficient forces and/or pressures, even the eversion-resistant feature will evert.

The eversion performance of a material can be characterized by its eversion pressure, which is the pressure required to evert a tube formed from the raw material. The eversion pressure is a measure of several properties of the material being affected at least by the material's stiffness and friction coefficient. Namely, raising either or both of a material's stiffness and friction coefficient yields higher material eversion pressures. Material stiffness is a function of at least the flexural modulus or hardness of the material and its wall thickness. The friction coefficient is also relevant because as the eversion starts, the material tends to roll at least partially upon itself. Once the material overlaps in this manner, any further movement requires that the material slide against itself. Thus, higher friction coefficient materials tend to increase frictional forces encountered by an everted sleeve, requiring increased forces to evert the materials once they have folded upon themselves.

The eversion-resistant feature may include one or more of the following attributes: increased stiffness or column strength, and an increased friction coefficient. An increased column strength resists that portion of the device 200 folding upon itself. Preferably, the length of this region 'L' is selected to allow at least a portion of the material to collapse fully on itself when a backpressure is applied. It is believed that such a collapse of the material forms a valve that can resist the pressure when the material is sufficiently stiff. The stiffness of the material is selected to promote its collapse and the formation of a valve at pressures at or near the eversion pressure of the otherwise unmodified raw sleeve material. To enable collapse upon itself, the length of the eversion-resistant feature 215 is greater than half the diameter of the internal lumen of the anchor 205 (i.e., L>D/2). Ideally, the eversion-resistant feature 215 also promotes collapse of the sleeve towards the elongated sleeve's central axis to prevent eccentric eversions.

One means of increasing the stiffness along the length of the eversion-resistant section 215 is to increase the material thickness. Increasing the thickness can be accomplished by layering the sleeve material upon itself until the desired thickness is attained. In some embodiments, the sleeve-anchoring device is encapsulated within two layers of sleeve material. Simply extending the region of the overlap a predetermined distance beyond the anchor itself provides a nice means of combining such functions. Alternatively, the eversion-resistant feature 215 can be formed using a second material having a higher modulus, thereby creating a relatively stiffer section.

Yet another means of increasing the material stiffness is providing reinforcing members coupled to the eversion-resistant section. For example, stiffness is increased by coupling one or more soft guidewires to the sleeve 210. At least one way to couple reinforcing members is to encase them within inner and outer layers of the sleeve material. Such an approach reduces the possibility that the reinforcing member will entrap chyme, impede peristalsis, and irritate the surrounding tissue. The guidewire provides linear stiffness thereby resisting buckling, while still allowing the section 215 to collapse and also providing little resistance to peristalsis. The guidewire is preferably oriented parallel to the central axis of the sleeve. The wire could be a vascular type guidewire commonly used to deliver catheters. These are typically constructed from stainless steel coils and having diameters between about 0.010 and 0.016 (i.e., 0.25 and 0.41 mm).

Materials such as soft, sticky silicone or polyurethane may be used in the anti-eversion feature 215. In some embodiments, one or more less-slippery materials are provided as a coating to the sleeve material. Alternatively or in addition, the friction coefficient of the eversion-resistant feature is increased by including a textured surface. Similarly, as the textured material collapses upon itself and attempts to roll inside out, the textured surface rubs against an adjacent surface to resist further sliding of the materials.

An exemplary embodiment of an implant device includes a sleeve formed from an ePTFE/FEP bi-laminate material available from W. L. Gore & Associates Medical Products Division, Flagstaff, Ariz. The sleeve is formed having an internal diameter of about 1 inch (i.e., about 25 mm) with an unmodified eversion pressure of about 3-7 inches $H_2O$. For the purposes of the testing, the length L of the eversion-resistant feature of the device was about 1.25 inches (i.e., about 3.2 cm) long. Additionally, the eversion-resistant feature was linearly tapered along its length from about 50 mm to about 25 mm in diameter. The number of layers of material used was varied from 2 covering the anchor, to 2 at the transition from the anchor to the tube, to 3 in the tube section. Each layer of material was about 0.0004 inches (i.e., about 0.0102 mm) thick. This construction resulted in an eversion pressure of the strain relief section of at least 30 inches $H_2O$ but preferably 40-60 inches $H_2O$. Preferably, transition from the anchor to the sleeve is accomplished in a gradual manner. For example, the transition includes staggering the thickness changes.

In some embodiments, the thickness of the eversion-resistant section is 0.002-0.004 inches (i.e., about 0.051 to 0.102 mm) and requires about 4-8 layers of the base material. This construction results in an eversion pressure of the strain relief section of at least 30 inches $H_2O$. Devices have been made with pressures of 60 inches $H_2O$. The target specification is preferably between about 35-55 inches $H_2O$.

Animal testing in a porcine model has demonstrated that using a device having a concentric eversion pressure of 30-60 inches $H_2O$, eliminated the occurrence of concentric eversions. However, a new failure mode was observed during testing, which is referred to as eccentric eversion. Several attributes of the test devices appeared to contribute to the eccentric eversions.

The transition region became substantially stiffer as more layers of material were applied. Also, the surface area of the anchor increased as the relaxed diameter increased from 50 mm to 60 mm. This increases the effective force acting on the anchor legs due to the pressure within the duodenum. With sufficient forces, one or more of the anchor legs can be pushed away from the wall of the duodenum. With the anchor deformed in this manner, the relatively stiff reinforced sleeve section may bend in the direction of the pressure towards the opening formed by the moved anchor leg. Thus, the net result of increasing the stiffness of the transition region too much for a given stiffness of the anchor can lead to an increased susceptibility to eccentric eversions.

Susceptibility to eccentric eversion can be improved by decreasing the relative stiffness of the transition region while maintaining the increased relative stiffness of the proximal sleeve. For example, stiffness of the transition was decreased by providing only 2 layers of the sleeve material; whereas, the relative stiffness of the first 1-2 inches of the 25 mm tube was increased by adding 3 layers of the same material in that region. Beneficially, the resulting eversion pressure remains between about 30 and 60 inches $H_2O$ while the likelihood of eccentric eversions is substantially reduced. Also, the softer transition region promotes collapse of the region concentrically, thereby preventing it from falling towards a side potentially leading to an eccentric eversion.

Thus, an eversion resistant section is formed as a compound element consisting of at least two sections. The first can be a tapered section that transitions from the 50 mm anchor to the 25 mm sleeve. This section serves several purposes. First, it makes the transition in diameters. Additionally, it serves as a so-called low-pressure "crumple zone." In other words, it collapses concentrically at low pressure without pulling the anchor away from the tissue surfaces. Preferably, the length of the crumple zone is no longer than the length of the anchor to avoid the crumple zone everting through the anchor. In some embodiments, the length of the crumple zone is about half the diameter of the sleeve. Then the second section is the stiffened sleeve section, which is drawn towards the center of the lumen by the collapse of the crumple zone. This area is stiff and therefore resists concentric eversion. This section may be tapered from 3 layers to 1.

Figure 3A:
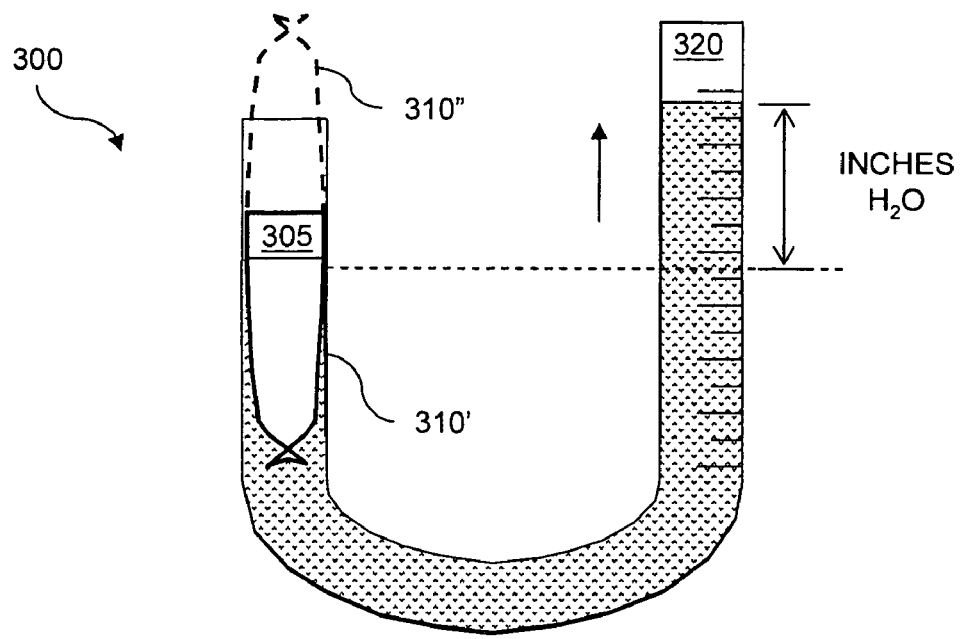
FIG. 3A is schematic diagram of an eversion pressure measurement test setup.

Measurement of concentric eversion-threshold pressure can be performed using a water-based test configuration measuring directly the inches of $H_2O$ required to evert the device. As shown in FIG. 3A, the anchor 305 of a 25 mm diameter device is sealably attached to the interior of a 25 mm diameter silicone tube 320. The attached sleeve 310' is tied off at some distance from the anchor 305 (e.g., about 6 inches from the anchor). The closed sleeve is extended within the tube 320 distal to the anchor 305. The tube 320 is bent into a 'U' shape with the device being placed in one of the vertical legs with other vertical leg being left open.

In operation, the tube 320 is partially filled with water from its open end. The water in the tube 320 represents a column of water applied to the distal side of the anchor 305. The open end of the tube is then raised with respect to the device, such that the potential energy of the displaced water provides a retrograde pressure upon the sleeve 310'. At some height, the sleeve 310" everts through the anchor 305 as shown in phantom. The corresponding height of the water at which the sleeve 310" everted is recorded as the corresponding eversion pressure in inches $H_2O$.

Another method of measuring concentric eversion-threshold pressure uses air rather than water. Air is preferred as it does not contaminate the tested materials, such that they can then be later used for implant. This set up is used to test the eversion pressure of either the raw material or the finished device. Raw material may be tested as an incoming quality assurance inspection to ensure consistency of the material. The overall concept described below is similar to the water-based test configuration.

Figure 3B:
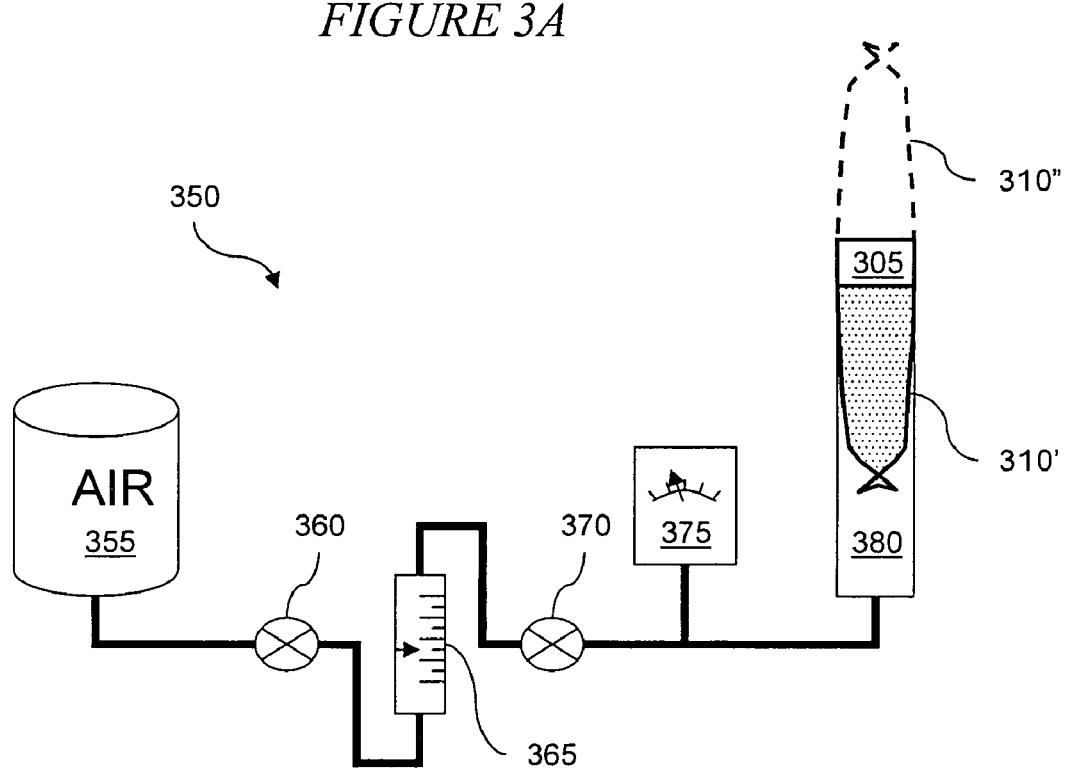
FIG. 3B is schematic diagram of an alternative eversion pressure measurement test setup.

Referring to FIG. 3B, the anchor 305 of a 25 mm diameter device is sealably attached to the interior of a 25 mm diameter silicone tube 380. The attached sleeve 310' is tied off at some distance from the anchor 305 (e.g., 6 inches from the anchor). The closed sleeve 310' is then extended within the tube 380 distal to the anchor 305. Air is supplied to the bottom of the tube 380 from a regulated air supply 355, such as a regulated air compressor through a flow-control system. The output of the air supply 355 is coupled through a needle valve 360 to one end of a flow meter 365. The other end of the flow meter 365 is coupled to one end of a check valve 370. The other end of the check valve is coupled to one end of the tube 380. A pressure-measuring device, such as a manometer 375 is coupled between the check valve 370 and the tube 380 to measure the pressure applied to the tube.

In operation, the check valve 370 is closed while a device under test is inserted into the tube 380. The device under test may be either samples of raw sleeve material or finished implants including eversion-resistant features. The needle valve 360 may be set to a pre-established flow rate such that the pressure will rise within the tube at a desired rate (i.e., not too fast to allow an operator to record pressure readings from the manometer 375. The check valve 370 is opened applying air pressure to the tube 380. As the pressure increases above the eversion-threshold pressure, the sleeve 310" will evert through the center of the anchor 305 as shown in phantom. The corresponding maximum pressure at which the sleeve everted is recorded as the corresponding eversion pressure.

Either test configuration may be used to measure corresponding eversion pressures of devices with or without eversion-resistant features. Thus, comparative results between the two measurements provides a performance measure of any improvement provided by the eversion-resistant feature.

In some embodiments as shown in FIG. 4A, an implant device 400 includes an anchor 405 defining an interior lumen having a first diameter $D_1$ coupled to a sleeve 410 defines an interior lumen having a second diameter $D_2$. For example, the anchor includes a first diameter that is greater than the sleeve's diameter (i.e., $D_1 > D_2$). This configuration is advantageous at least in gastrointestinal applications in which a seal between the anchor and the body lumen is desired. Thus, the anchor 405 functions in part as a radial spring, providing an outward force against the surrounding tissue when implanted. In order to provide the outward force, the resting diameter of the anchor is larger than the diameter when implanted.

A tapered eversion-resistant feature 415 can be applied between the anchor 405 and the sleeve 410, the feature 415 providing a transition from one diameter to another. For example, the eversion-resistant feature 415 is an open cone transitioning from $D_1$ to $D_2$. The eversion-resistant feature 415 can include any of the properties described above including increased stiffness and/or friction coefficient. Similarly, these properties can be applied using any of the techniques described herein, the main difference being the tapered shape of the resulting treated area.

FIG. 4B illustrates deformation of the eversion-resistant feature 415 when subjected to retrograde pressures. Preferably, the eversion-resistant feature 415 collapses upon itself whereby the material properties resist eversion thereby blocking any opening through which the distal sleeve 410 may evert.

Figure 5A:
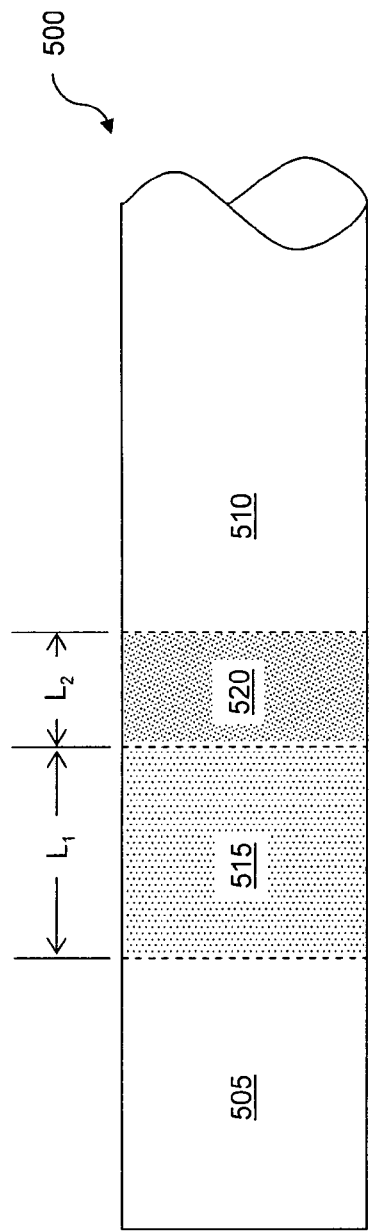
FIGS. 5A and 5B are schematic diagrams of an exemplary implantable anchored sleeve according to one embodiment of the invention having an eccentric-eversion resistant feature.
Figure 5B:
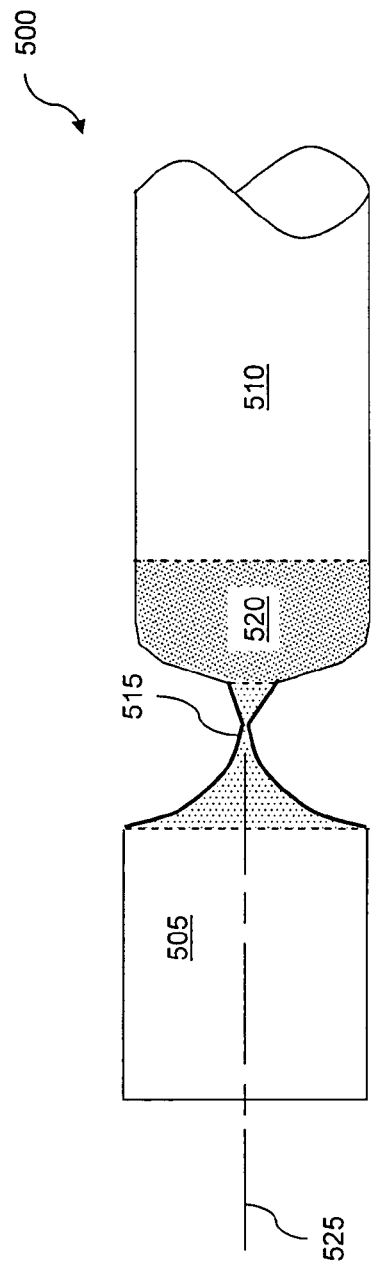

In some embodiments, an eversion-resistant feature is provided as a compound element providing different properties along different portions of the treated surface area. As shown in FIGS. 5A and 5B, an implant device 500 includes a proximal anchor 505 and a distal sleeve 510. The eversion-resistant feature provided between the anchor 505 and the sleeve 510 is applied resulting in at least two distinguishable regions. A proximal region 515 extends distally for a first length $L_1$ from the distal end of the anchor 505. A distal region 520 extends distally from the first region 515 for a second length $L_2$. The raw sleeve material extends distally from the distal end of the second region.

Such a compound eversion-resistant feature can provide eversion-resistance to both concentric eversions and to eccentric eversions. For example, the proximal region 515 can be configured as a so-called "crumple zone." As the name suggests, when subjected to sufficient retrograde pressures, the proximal region 515 collapses upon itself as described above in reference to FIGS. 2 and 4. The distal region 520 can be configured as a so-called reinforced region having a higher eversion-resistance than the proximal region 515 to resist crumpling at the same pressure. The initial collapse of the proximal region 515 tends to center the distal region 520, such that further collapse of that region occurs towards the center rather than along the edge as the retrograde pressure continues to increase. Collapse of the distal region 520 ultimately blocks the central lumen without everting fully, thereby prohibiting further eversion of the sleeve 510 through the blocked lumen.

Figure 6A:
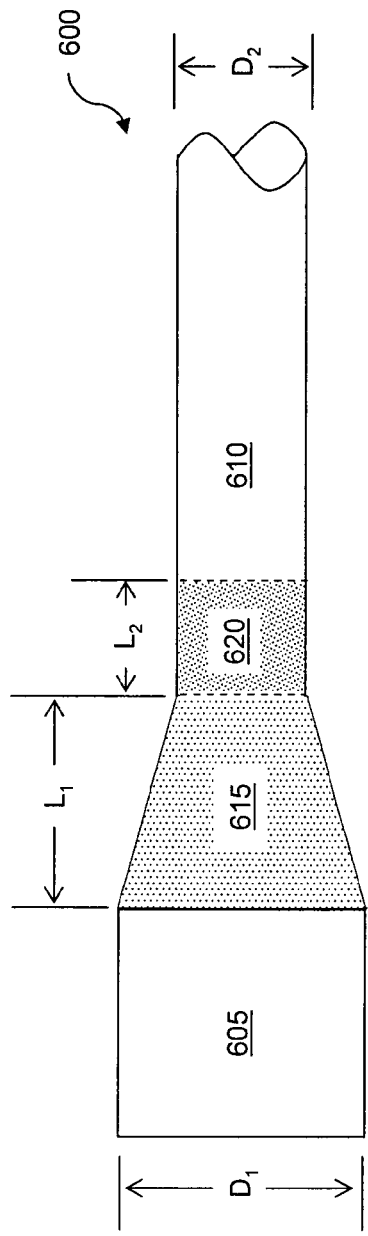
FIGS. 6A and 6B are schematic diagrams of an exemplary implantable anchored sleeve according to one embodiment of the invention having a tapered section and an eccentric-eversion resistant feature.
Figure 6B:
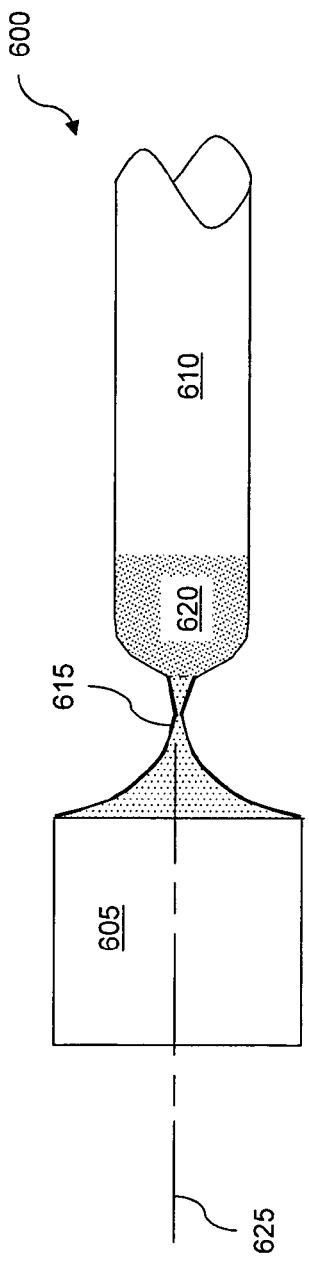

A tapered device having a compound eversion-resistant feature is illustrated in FIGS. 6A and 6B. The device 600 includes a proximal anchor having a first diameter $D_1$ (e.g., about 50 mm) coupled through an eversion-resistant feature to the proximal end of an elongated sleeve having a second diameter $D_2$ (e.g., about 25 mm). Typically, the sleeve's diameter is less than that of the anchor 605 (i.e., $D_1 > D_2$). The compound eversion-resistant feature includes a proximal region 615 extending for a first length $L_1$ (e.g., about 1.5 inches) followed by a distal region 620 extending for a second length $L_2$ (e.g., about 1.0 inch).

The proximal region 615 can be configured as a crumple zone and the distal region 620 can be configured as a reinforced region. In the presence of sufficient retrograde pressures, the proximal region 615 collapses upon itself first while the distal region remains substantially open. As the pressure continues to increase, the distal region 620 also collapses upon itself, being substantially centered by the initially-collapsed crumple zone 615, thereby avoiding an eccentric eversion.

In some embodiments, tapering from the first $D_1$ to $D_2$ is accomplished in the proximal region 615. It is believed that applying a taper to this region may further enhance performance of the eversion-resistant feature by focusing collapse of the material towards the device's longitudinal axis.

Figure 7A:
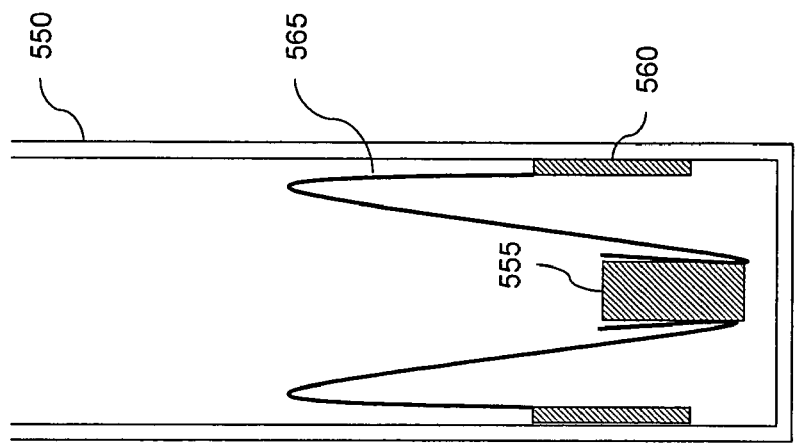
FIGS. 7A and 7B are schematic diagrams of an eccentric eversion measurement test setup.
Figure 7B:
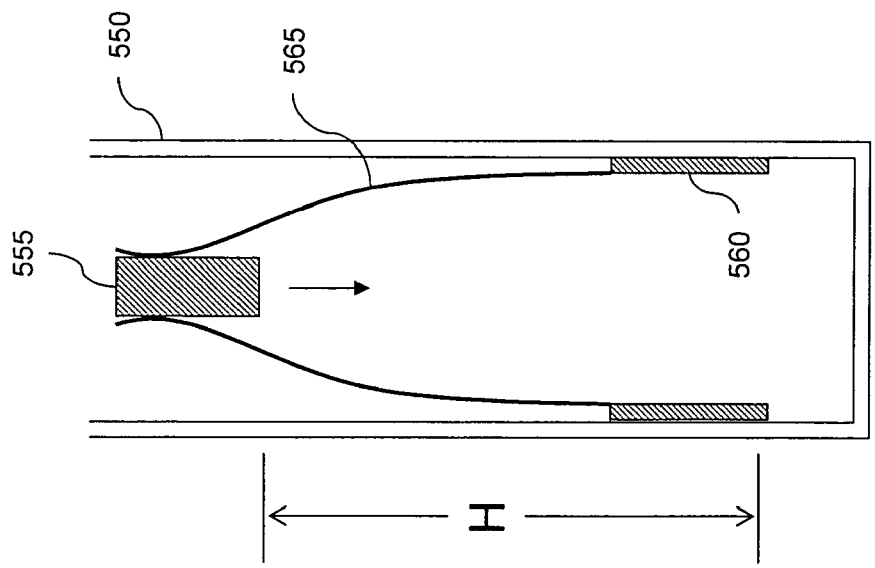

Measurement of eccentric eversion susceptibility can be accomplished using an eccentric-measurement test setup. An exemplary test setup is illustrated in FIGS. 7A and 7B. The anchor of an implant device under test is coupled to the interior of a large-diameter silicon tube (e.g., about 40 mm for a 50 mm diameter anchor). A weight is then attached to a distal end of the sleeve at a predetermined distance from the anchor. The weight is raised above the anchor to fully extend the sleeve. For example, the weight can be a metal rod that is placed inside the sleeve, coupled to the sleeve, and dropped from a height of about 6 inches (i.e., about 15 cm) towards the anchor. The metal rod is relatively narrow. For example, a metal rod about 0.5 inches (i.e., about 13 mm) in diameter that weighs about 0.6 pounds (i.e., 0.23 kg) was used for test results provided herein.

The weight is dropped towards the anchor and depending upon the device under test, the weight may travel through the center of the anchor resulting in a concentric eversion, or the weight may travel towards a side of the anchor resulting in an eccentric eversion. The test is repeated a predetermined number of times for the same device under test. Eccentric eversion susceptibility is determined as the percentage of total tries resulting in an eccentric eversion.

Thus, this test can be used to measure the eccentric eversion susceptibility of different devices and is useful in identifying features that reduce or eliminate the eccentric eversion failure mode. Four different devices were tested using the test configuration of FIGS. 7A and 7B. The devices are described in Table 1.

TABLE 1

Devices Under Test

| Design # | Anchor design | Eversion design | Material thickness | Layering method |
|---|---|---|---|---|
| 1 | 60 mm OD × 0.020" wire diameter | Single cone transition element and short cylinder | 0.0010"-0.0015" | Wrapped |
| 2 | 50 mm OD × 0.023" wire diameter | Single cone transition element | 0.0015"-0.0020" | Template |
| 3 | 50 mm OD × 0.023" wire diameter | Single cone transition element and short cylinder | 0.0010"-0.0015" | Wrapped |
| 4 | 50 mm OD × 0.023" wire diameter (most recent design) | Single cone transition element and long cylinder | Cone is 2 layers (0.0010") Cylinder is 3 layers (0.0015") | Template |

Exemplary data resulting from 30 attempts per device for each of the 4 different devices is summarized in Table 2.

TABLE 2

Eccentric Test Results

| Device | Concentric | Eccentric | % Eccentric |
|---|---|---|---|
| Design 1 | 20 | 10 | 33.3% |
| Design 2 | 13 | 2 | 13.3%* |
| Design 3 | 30 | 0 | 0% |
| Design 4 | 30 | 0 | 0% |

*15 tries only - device broke

These tests showed that the eversion-resistant features of devices 3 and 4 are much less susceptible to the eccentric-eversion failure mode. These data also are supported by animal evaluations. Designs 1 and 2 had high rates of eccentric eversion in pigs. Design 3 was an early design in which eversions were very rare. Design 4 has also resulted in a device in which eversions are rare in animal testing.

Figure 8:
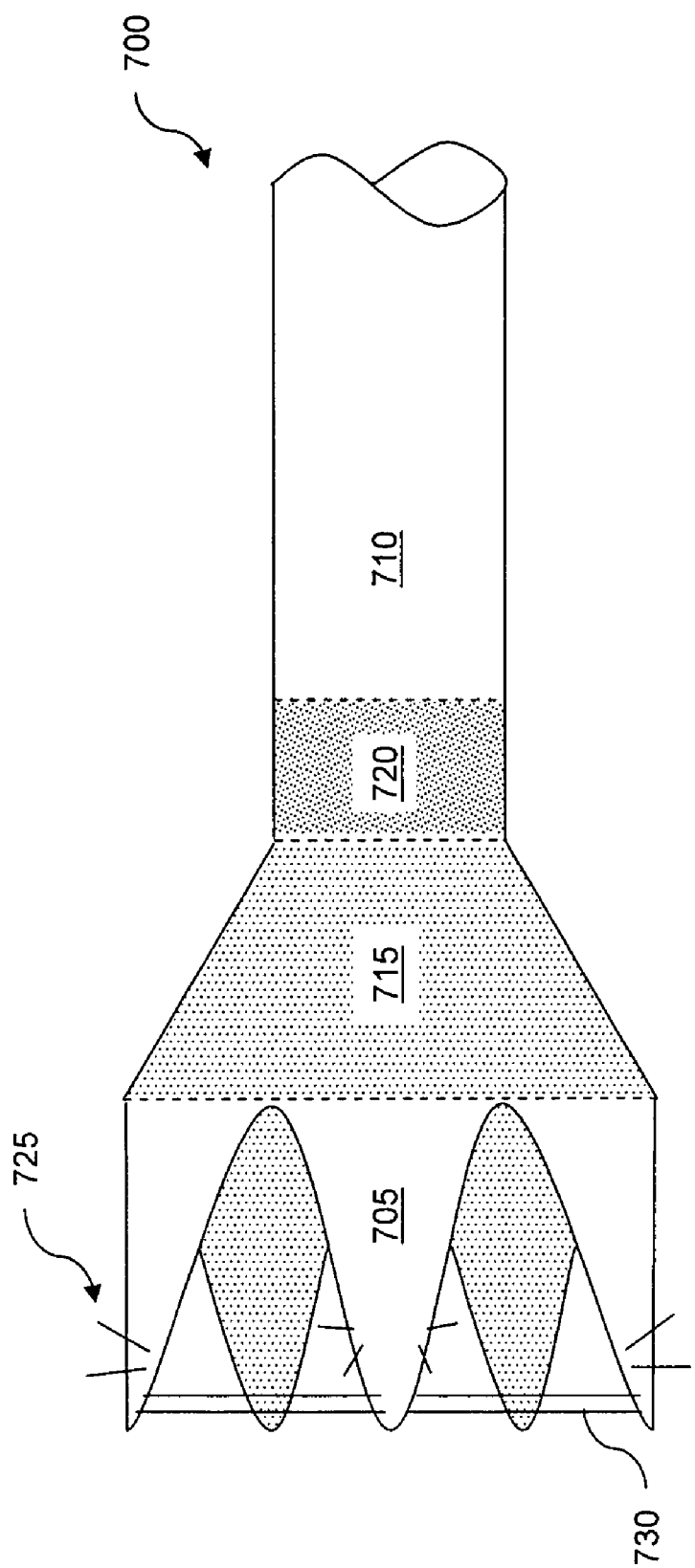
FIG. 8 is schematic diagram of an exemplary embodiment of an implantable anchored sleeve including an eccentric eversion resistant feature and a wave anchor.

An embodiment combining a wave anchor with a compound eversion-resistant feature is illustrated in FIG. 8. The device is similar to that described above in reference to FIG. 6A in that it includes a proximal anchor 705 having a first diameter and a distal elongated sleeve 710 having a second diameter less than the first. A compound eversion-resistant feature includes a proximal region 715 adjacent to the anchor and tapered between the first and second diameters. A reinforced region 720 is provided between the proximal region 715 and the proximal sleeve 710. The anchor 705, however, is illustrated in more detail. In particular, the anchor can be a wave anchor defining multiple oscillations about a central lumen as described in U.S. application Ser. No. 10/858,852, filed on Jun. 1, 2004, and entitled "Method and Apparatus for Anchoring Within the Gastrointestinal Tract" incorporated herein by reference in its entirety. As shown, the proximal portion of the sleeve can be tailored to the boundary defined by the anchor resulting in the tulip-petal shape. The anchor, when implanted is reduced in diameter slightly by the local anatomy of the body lumen. Beneficially, the outward radial spring force provided by the partially-compressed anchor results in a sealable connection between the proximal end of the device and the interior surface of the body lumen.

The spring force of the anchor provides some anchoring force to maintain the anchor in a predetermined location. However, the anchor can be attached to the local anatomy using one or more external connecting means. For example, the anchor can be sutured in place, coupled using surgical staples, and/or coupled using surgical adhesives. Preferably, the anchor is attached to the anatomy in a removable fashion. For example, the anchor can optionally include one or more barbs 725 or spines protruding outward and adapted to engage the surrounding muscular tissue.

Alternatively or in addition, the device can include one or more features adapted to facilitate removal of the device. For example, the device can include one or more drawstrings 730 at its proximal end. The drawstrings are slideably attached to the proximal ends of the anchor and are adapted to centrally collapse the anchor when suitably engaged. Preferably, the collapse pulls any barbs out of the surrounding tissue prior to removal to avoid unnecessary tissue damage. A separate removal device can then be used to remove the device as described in pending U.S. Provisional Application No. 60/663,352, filed on Mar. 17, 2005, and entitled "Removal and Repositioning Devices," incorporated herein by reference in its entirety.

Figure 9:
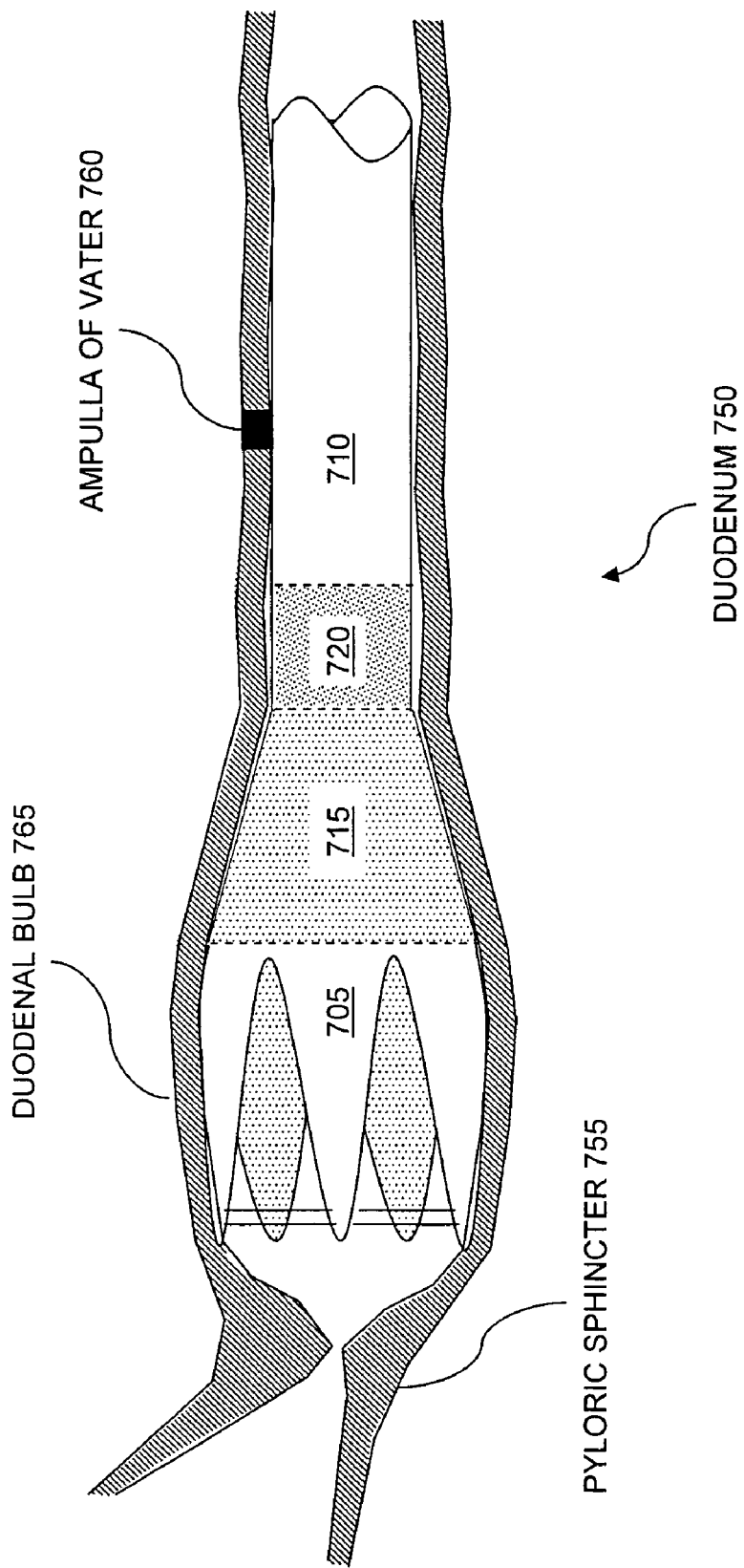
FIG. 9 is cross-sectional schematic diagram of a portion of the gastrointestinal tract illustrating the location of the exemplary implantable sleeve of FIG. 8.

FIG. 9 shows a cross-sectional view of a portion of a duodenum 750 with a device implanted therein. The anchor 705 is situated in the proximal duodenum in an area referred to as the bulbous duodenum 765, located distal to the pyloric sphincter 755 and proximal to the ampulla of vater 760. The anchor 705 is partially compressed resulting in a fluid seal between it and the surrounding intestine wall. The sleeve 710 extends distally into the duodenum 750 and, depending upon its length, beyond the duodenum into distal parts of the small intestine not shown.

Figure 10:
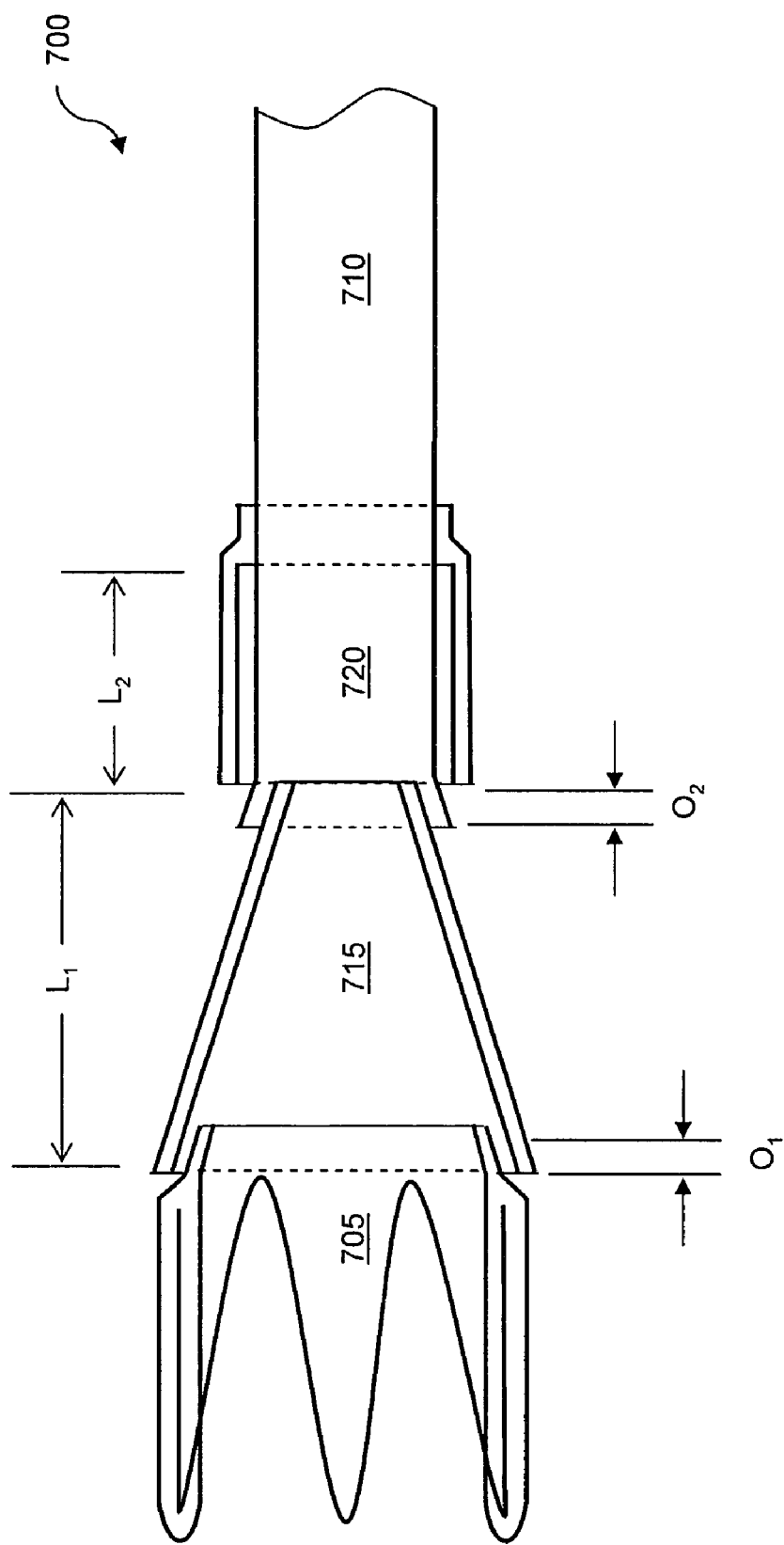
FIG. 10 is cross-sectional schematic diagram of an exemplary embodiment of an implantable anchored sleeve including an eccentric eversion resistant feature.

FIG. 10 shows a cross section of one embodiment of the sleeve 700 shown in FIG. 9 using overlapping material to form the different regions of the compound eversion feature. Starting at the proximal end, a wave anchor 705 is surrounded by an inner and outer layer of the sleeve material. The proximal anti-eversion region 715, or tapered crumple zone, is similarly formed using two layers of the same sleeve material. Preferably, some amount of overlap $O_1$ is provided to facilitate attachment of the covered anchor 705 to the proximal end of the crumple zone 715. For example, the two regions may be attached using an adhesive. Alternatively or in addition, the two regions may be attached using a mechanical fastener such as a suture. Preferably, however, thermal boding is used to sealably connect the two regions together along the periphery of the device within the overlapping region $O_1$.

A proximal end of the sleeve similarly overlaps a distal end of the crumple zone by a length $O_2$ to facilitate attachment of the two regions. Any of the above means of attaching can be used to form the attachment. A second and third layers are added just distal to the end of the crumple zone 715, thereby forming a reinforced region 720 having three layers of sleeve material. As shown, the outer-most layer 725 of the reinforcing region 720 may extend beyond the second layer 727 and attach to the outer surface of the sleeve 710 to form a smooth transition.

Although a gastrointestinal sleeve is described as an exemplary embodiment, other applications include arterial grafts, esophageal prostheses, and other gastrointestinal prostheses, such as biliary sleeves.

While this invention has been particularly shown and described with references to preferred embodiments thereof, it will be understood by those skilled in the art that various changes in form and details may be made therein without departing from the scope of the invention encompassed by the appended claims.

What is claimed is:

1. A device for implanting within an animal body comprising:
   a proximal anchor adapted for attachment within a natural body lumen;
   a thin-walled sleeve open at both ends and defining a lumen therebetween, a proximal end of the sleeve being coupled to the anchor, a substantial length of the sleeve being a floppy zone having material characteristics that result in the sleeve being prone to eversion;
   an eversion-resistant feature of the sleeve disposed only at the proximal end of the sleeve that inhibits eversion of the sleeve by collapsing radially in the presence of retrograde pressures, the floppy zone of the sleeve extending the substantial length of the sleeve beyond the eversion resistant feature, the eversion-resistant feature comprising:
      a proximal crumple zone of the sleeve that collapses radially in the presence of retrograde pressures; and
      a distal reinforced region of the sleeve between the crumple zone and the floppy zone of the sleeve, the reinforced region collapsing radially, but to a lesser extent than the crumple zone, in the presence of retrograde pressures.

2. The device of claim 1, wherein the eversion-resistant feature comprises increased stiffness relative to the sleeve's stiffness.

3. The device of claim 2, wherein the increased stiffness is provided by a different material than that of the sleeve.

4. The device of claim 2, wherein the increased stiffness is provided by an increased wall thickness of the same material relative to that of the sleeve.

5. The device of claim 4, wherein the increased wall thickness comprises more than one layer of material.

6. The device of claim 2, wherein the increased stiffness is provided by a reinforcing member.

7. The device of claim 1, wherein a surface of the eversion-resistant feature has a coefficient-of-friction greater than that of a corresponding surface of the sleeve.

8. The device of claim 7, wherein the eversion-resistant feature comprises a different material having a coefficient of friction greater than that of the thin-walled, floppy sleeve.

9. The device of claim 7, wherein at least a portion of the exterior surface of the eversion-resistant feature is textured.

10. The device of claim 1, wherein the crumple zone comprises a tapered cone defining a proximal opening having a first diameter and a distal opening having a second diameter less than the first, a sufficient retrograde pressure moving the distal opening proximally while inhibiting lateral movement towards the walls of the body lumen.

11. The device of claim 1, wherein the eversion-resistant element is adapted to partially collapse upon itself thereby forming a valve allowing flow in an antegrade direction, while prohibiting flow in a retrograde direction thereby blocking eversion of the sleeve.

12. The device of claim 1, wherein the device has a concentric eversion pressure of at least 30 inches $H_2O$.

13. A method for inhibiting eversion of a sleeve device when implanted within a natural body lumen comprising:
   providing an eversion-resistant feature of a thin-walled sleeve only at a proximal end of the sleeve, the eversion-resistant feature having an eversion-threshold pressure greater than that of the sleeve itself, a floppy zone of the sleeve extending a substantial length of the sleeve beyond the eversion-resistant feature;
   anchoring, with an anchor, the proximal end of the sleeve with the eversion-resistant feature in the lumen;
   focusing collapse of the eversion-resistant feature towards the longitudinal axis of the anchor by radially collapsing a proximal crumple zone of the sleeve in the presence of retrograde pressures; and
   radially collapsing a distal reinforcing region of the sleeve coupled to the proximal crumple zone of the sleeve in the presence of retrograde pressures, the distal reinforcing region collapsing to a lesser extent than the proximal crumple zone.

14. The method of claim 13, further comprising the steps of increasing the stiffness of a proximal portion of the thin-walled, floppy sleeve.

15. The method of claim 14, wherein the step of increasing the stiffness comprises providing a different material relatively stiffer than the sleeve.

16. The method of claim 14, wherein the step of increasing the stiffness comprises providing more than one layer of material.

17. The method of claim 16, wherein the step of increasing the stiffness comprises coupling a reinforcing member to the proximal end of the sleeve.

18. The method of claim 13, further comprising the steps of increasing the coefficient of friction along an exterior surface a proximal portion of the thin-walled, floppy sleeve.

19. The method of claim 18, wherein the step of increasing the coefficient of friction comprises providing a different material.

20. The method of claim 18, wherein the step of increasing the coefficient of friction comprises texturing the exterior surface.

21. The method of claim 13, further comprising the step of inducing a partial collapse of the eversion-resistant element upon itself, thereby forming a valve allowing flow in an antegrade direction, while prohibiting flow in a retrograde direction in the presence of retrograde pressures.

22. A device for implanting within an animal body comprising:
   means for anchoring a proximal end of the device within a natural body lumen, the device including an elongated, thin-walled sleeve open at both ends and defining a lumen therebetween, a floppy zone of the sleeve having material characteristics that result in the sleeve being prone to evert proximally to the anchor;
   eversion resisting means of the sleeve for resisting eversion of any portion of the sleeve proximally to the anchoring means by collapsing radially in the presence of retrograde pressures, the eversion resisting means being disposed only at a proximal end of the sleeve, a floppy zone of the sleeve extending a substantial length of the sleeve beyond the eversion resisting means, the eversion resisting means comprising:
- a proximal crumple zone of the sleeve that collapses radially in the presence of retrograde pressures; and
- a distal reinforcing region of the sleeve coupled to the crumple zone, the reinforcing means collapsing radially, but to a lesser extent than the crumple zone, in the presence of retrograde pressures.

23. A device for implanting within an animal body comprising:
- an anchor adapted for attachment within a natural body lumen;
- a thin-walled, floppy sleeve open at both ends and defining a lumen therebetween, a substantial length of the sleeve having material characteristics that result in the sleeve being prone to eversion;
- an eversion-resistant feature disposed between the anchor and the proximal end of the sleeve that inhibits eversion of the sleeve by collapsing radially in the presence of retrograde pressure, the eversion-resistant feature comprising:
- a proximal crumple zone of the sleeve that collapses in the presence of retrograde pressures; and
- a distal reinforced region of the sleeve between the crumple zone and the substantial length of the sleeve, the reinforcing means collapsing, but to a lesser extent than the crumple zone, in the presence of retrograde pressures.

24. The device of claim 23, wherein the crumple zone comprises a tapered cone defining a proximal opening having a first diameter and a distal opening having a second diameter less than the first, a sufficient retrograde pressure moving the distal opening proximally while inhibiting lateral movement towards the walls of the body lumen.

25. The device of claim 23, wherein the device has a concentric eversion pressure of at least 30 inches $H_2O$.

* * * * *